United States Patent [19]

Balakian

[11] Patent Number: Plant 6,025

[45] Date of Patent: Sep. 29, 1987

[54] PEACH TREE (B-41871)

[75] Inventor: Leo Balakian, 41871 Rd. 52, Reedley, Calif. 95654

[73] Assignees: Leo Balakian; Rosalie Balakian, both of Fresno, Calif.

[21] Appl. No.: 772,934

[22] Filed: Sep. 5, 1985

[51] Int. Cl.[4] ..... A01H 5/03

[52] U.S. Cl. ..... Plt./43

[58] Field of Search ..... Plt./43

*Primary Examiner*—Robert E. Bagwill

*Attorney, Agent, or Firm*—Dennison, Meserole, Pollack & Scheiner

[57] ABSTRACT

A new and distinct variety of peach tree which is large, vigorous, upright, spreading and hardy under California conditions; foliated with medium to large, lanceolate leaves having a crenate to finely serrate margin, and alternate globose glands; and is a regular and productive bearer of large, early ripening, uniform, semi-freestone, very slightly asymmetrical fruit globose in apical aspect and globose to slightly ovoid in lateral aspect, the fruit having straw-yellow ground color blushed with red, and yellow-amber flesh color.

1 Drawing Figure

BACKGROUND OF THE VARIETY

Field of the Invention

As an owner of a ranch, including orchards, located near Reedley, Fresno County, Calif., I frequent such ranch and orchards for the purpose of inspection, and the supervision of soil cultivation, irrigation, and harvesting of crops. Against this background of my activities, the present variety of peach tree was discovered by me.

CLASSIFICATION OF THE VARIETY

The present variety of peach tree is embraced by Class 43, Plants, of the U.S. Patent Office Manual of Classification.

PRIOR VARIETIES

Among existing varieties of peach trees which are known to me is the Maycrest (U.S. Plant Pat. No. 4,064), and which variety is mentioned herein for the purpose of comparison.

ORIGIN OF THE VARIETY

The present variety of peach tree was discovered by me in an orchard of Maycrest trees on my ranch located aforesaid; my discovery of the present variety having been made during routine orchard operations and just prior to harvest of the Maycrest trees. During such operations, I recognized that one tree in the orchard was distinctive in several respects. I subsequently maintained such tree under close, regular and continued observation; such observations having confirmed the distinctive characteristics of the present variety of peach tree—and which is believed to be a whole tree mutation of the Maycrest. I, therefore, determined to asexually reproduce the present variety of peach tree with a view toward the ultimate commercial growth thereof.

ASEXUAL REPRODUCTION OF THE VARIETY

The present variety of peach tree was asexually reproduced, under my direction, by budding on existing and compatible peach rootstock; such reproductions having been undertaken in my orchard, located as aforesaid, and in maturity the reproductions ran true in all respects to the original tree.

SUMMARY OF THE VARIETY

The present variety of peach tree is large, vigorous, upright, spreading and hardy under California conditions; foliated with medium to large, lanceolate leaves having a crenate to finely serrate margin, and alternate, globose glands; and is a regular and productive bearer of large, early ripening, uniform, semi-freestone, very slightly asymmetrical fruit globose in apical aspect and globose to slightly ovoid in lateral aspect, the fruit having straw-yellow ground color blushed with red, and yellow-amber flesh color.

The present variety of peach tree is further, and more particularly, characterized—in comparison to the Maycrest—by more vigorous tree growth; by above average uniformity of fruit distribution on the tree; by more advancement of the external color of the fruit in the early stages of ripening; and by ripening to picking maturity, of the semi-freestone fruit, approximately six days earlier. When both the Maycrest and the present variety reach maturity on their respective ripening dates, their external appearance is quite similar.

BRIEF DESCRIPTION OF THE DRAWING

The drawing is an illustration, by photographic reproduction in color, of a twig with leaves, separate leaves, and separate fruit of the present variety of peach tree; one of the fruit being half cut away to expose the flesh and with the stone remaining in place.

DESCRIPTION OF THE VARIETY

The botanical details of this new and distinct variety of peach tree—with color definitions (except those in common color terms) referenced to Maerz and Paul Dictionary of Color (1950 Edition)—are as follows:

Tree:

*Size.*—Large.

*Vigor.*—*Vigorous.*

*Growth.*—Upright. Spreading

*Hardiness.*—Hardy, under Central Valley conditions in California.

*Production.*—Productive.

*Bearing.*—Regular bearer.

Trunk:

*Size.*—Medium.

*Texture.*—Medium.

*Color.*—Mature Bark — Reddish-brown (8-C-10).

*Lenticels.*—Size: Moderately large. Number: Numerous. Color: Light brown (7-A-11) on corky lenticel surface.

Branches:

*Size.*—Medium.

*Texture.*—Medium.

*Color.*—Immature branches, light green (20-H-5). Mature branches, grey-brown (7-C-9).

*Lenticels.*—Number: Moderate. Size: Small.

Leaves:

*Size (at midpoint of actively growing shoots)*-.—Medium to large. Average length — 16.2 cm. Average width — 3.5 cm.

*Texture.*—Smooth.

*Form.*—Lanceolate. Tip acuminate.

*Color.*—Top side — Deep green (24-L-2). Under side — Grey-green (21-D-4).

*Margin.*—Mixed — Crenate (often doubly so) to finely serrate.

*Leaf edge.*—Moderately undulate.

*Petiole.*—Medium size. Length range — 7–10 mm. Thickness range — 1–1.5 mm. Light green (19-F-3).

*Glands.*—Medium size. Globose. Range number — 2–4, most commonly 2. Usually located at basal edge of leaf margin. Occasionally 1 or 2 glands are stalked. Alternate. Yellow-green (18-K-3) and shiny, but darkening with age.

*Stipules.*—Medium size. Light green (18-H-4). Early deciduous.

Fruit:

*Maturity when described.*—Firm ripe — May 15, 1985.

*Date of first picking.*—May 14, 1985.

*Date of last picking.*—May 17, 1985.

*Size.*—Large for early season of maturity. Uniform. Average suture diameter — 59 mm. Average cheek diameter — 60 mm. Average axial diameter — 56 mm.

*Fruit uniformity on tree.*—Above average.

*Form.*—Uniform. Slightly asymmetrical, with one-half of fruit slightly larger. Globose in apical aspect. Globose to slightly ovoid in lateral aspect.

*Suture.*—Distinct. Extends from base to apex with slight depression beyond pistil point. Conspicuous, but narrowing in width both basally and apically. Basal portion narrow with sides slightly folded together. Average width — 2–2.5 mm. at midpoint Straw-yellow (10-I-2). Suture usually without blush color.

*Ventral surface.*—Rounded. Very slightly lipped along entire surface, with one side usually slightly larger.

*Stem cavity.*—Broad. Shallow. Depth range — 10–11 mm. Average width — 24 mm. Average length — 26 mm. Round to slightly oblong in basal aspect. Suture visible only on ventral side of fruit.

*Base.*—Slightly truncate. Very slightly oblique to fruit axis.

*Stem.*—Average size and length. Length range — 8.5–9.0 mm. Average thickness — 3.0 mm. Light green (18-J-4).

*Apex.*—Rounded. Short.

*Pistil point.*—Variable, but most commonly slightly oblique and somewhat sharp.

Skin:

*Thickness.*—Average.

*Texture.*—Average.

*Tenacity.*—Tenacious to flesh until overripe.

*Tendency to crack.*—None observed.

*Pubescence.*—Light. Short fibers.

*Color.*—Ground color — Straw-yellow (10-H-3), most commonly located basally. Blush color — Dark red (7-L-10), especially over apex and areas exposed to direct sunlight. Washed Orange-red (5-K-11) to Light orange (4-G-11) over sides and basally. Some mottling and striping of blush color over sides and basally. Blush color commonly covers over one-half of fruit surface.

Flesh:

*Color.*—Yellow-amber (10-J-4). Uniform from edge of skin to pit cavity.

*Amygdalin.*—Slight to lacking.

*Juice.*—Moderate at firm ripe, increasing in amount as fruit softens.

*Flavor.*—Good. Mild. Well-balanced.

*Aroma.*—Slight.

*Texture.*—Medium to fine. Melting.

*Fibers.*—Medium number. Medium texture.

*Ripens.*—Evenly.

*Eating quality.*—Good, especially for early season of maturity.

Stone:

*Type.*—Semi-freestone. Very tight at commercial maturity.

*Size.*—Medium. Average length — 33 mm. Average width — 24 mm. Average thickness — 19 mm.

*Fibers.*—Average number. Medium length.

*Form.*—Oval to slightly ovoid.

*Base.*—Most frequently slightly oblique to fruit axis. Shortest on ventral suture edge.

*Hilum.*—Narrow. Oblong.

*Apex.*—Acute. Tip acuminate. Sharp.

*Sides.*—Nearly equal.

*Surface.*—Deeply grooved across apical shoulder. Shallow grooves over basal shoulder. Mid-stone pitted and somewhat grooved over lateral surfaces.

*Pits.*—Both circular and oval. Concentrated at mid-stone and basal areas.

*Ventral edge.*—Medium thickness. Low and thickened wing along basal shoulder of ventral suture. Wings converging apically.

*Dorsal edge.*—Moderately thick with deep groove from base to above mid-stone. Edges of groove irregular and roughened. Groove narrower and shallower over apical shoulder.

*Color.*—Light brown (10-H-4).

*Tendency to split.*—Slight.

Use: Dessert. Fresh market for both local and long distance shipping.

Keeping quality: Good.

Resistance to insects and diseases: No particular susceptibilities noted.

The peach tree and its fruit herein described may vary in slight detail due to climatic and soil conditions under which the variety may be grown; the present description being of the variety as grown in the Central Valley of California.

I claim:

1. A new and distinct variety of peach tree, substantially as illustrated and described, characterized—in comparison to the Maycrest—by more vigorous tree growth; by above average uniformity of fruit distribution on the tree; by more advancement of the external color of the fruit in the early stages of ripening; and by ripening to picking maturity of the semi-freestone fruit, approximately six days earlier.

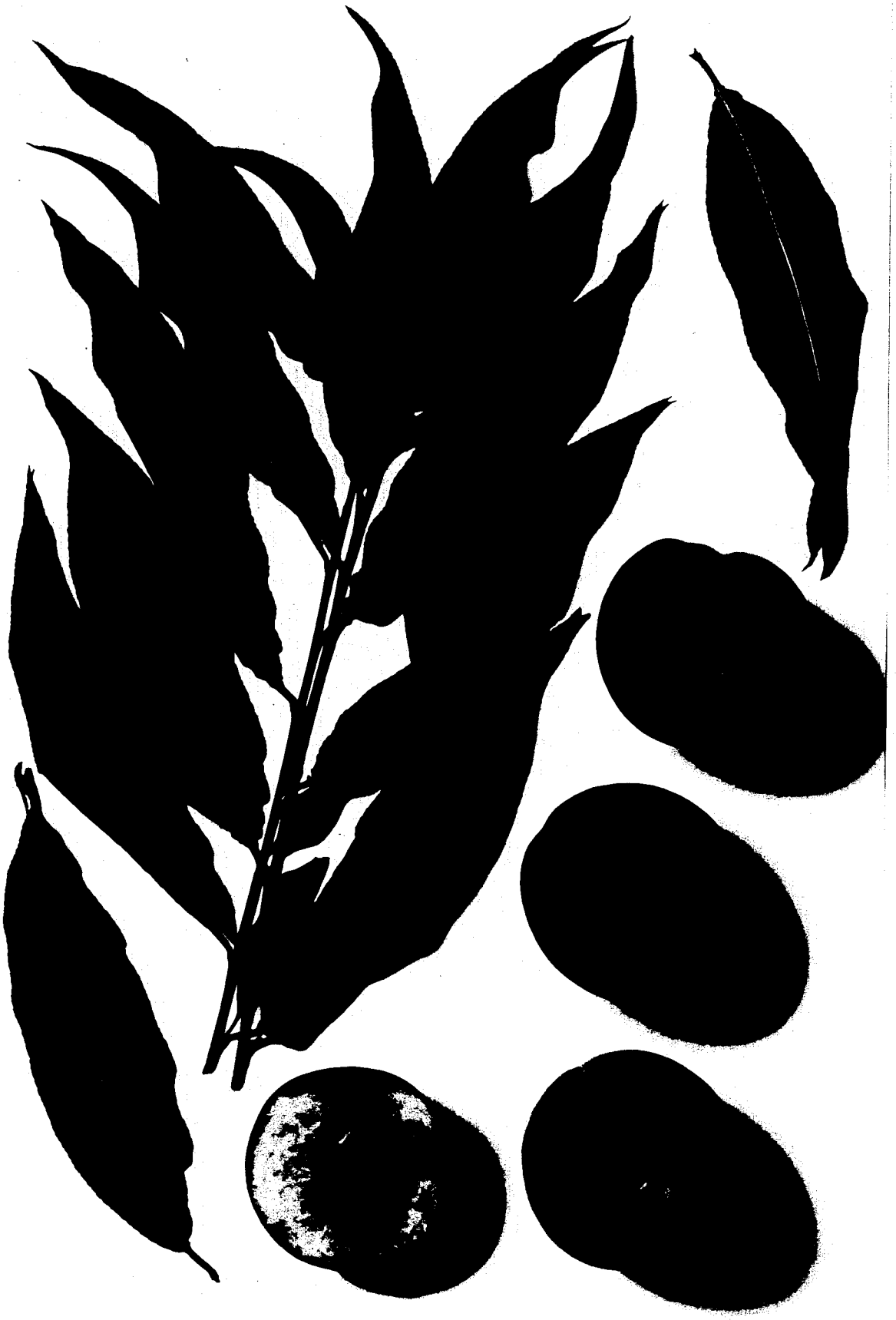

* * * * *